US006963768B2

(12) United States Patent
Ho et al.

(10) Patent No.: US 6,963,768 B2
(45) Date of Patent: Nov. 8, 2005

(54) WHOLE BODY MRI SCANNING WITH MOVING TABLE AND INTERACTIVE CONTROL

(75) Inventors: Vincent B. Ho, North Bethesda, MD (US); Thomas K. F. Foo, Potomac, MD (US)

(73) Assignee: General Electric Company, Milwaukee, WI (US)

( * ) Notice: Subject to any disclaimer, the term of this patent is extended or adjusted under 35 U.S.C. 154(b) by 396 days.

(21) Appl. No.: 10/063,829

(22) Filed: May 16, 2002

(65) Prior Publication Data

US 2003/0216637 A1 Nov. 20, 2003

(51) Int. Cl.[7] .............................................. A61B 5/05
(52) U.S. Cl. ...................................................... 600/415
(58) Field of Search .................................. 600/415, 416, 600/410, 407; 378/20, 68, 69; 18/177; 324/307, 308, 309, 300; 5/601, 600

(56) References Cited

U.S. PATENT DOCUMENTS

| | | | | |
|---|---|---|---|---|
| 5,584,293 A | * | 12/1996 | Darrow et al. | 600/410 |
| 5,631,560 A | * | 5/1997 | Machida | 324/309 |
| 5,671,741 A | * | 9/1997 | Lang et al. | 600/415 |
| 5,928,148 A | | 7/1999 | Wang et al. | |
| 6,317,620 B1 | | 11/2001 | Ho et al. | |
| 6,385,481 B2 | * | 5/2002 | Nose et al. | 600/415 |
| 6,425,864 B1 | * | 7/2002 | Foo et al. | 600/420 |
| 6,490,476 B1 | * | 12/2002 | Townsend et al. | 600/427 |
| 6,535,821 B2 | * | 3/2003 | Wang et al. | 702/19 |
| 6,564,085 B2 | * | 5/2003 | Meaney et al. | 600/415 |
| 6,580,937 B2 | * | 6/2003 | Ho et al. | 600/415 |
| 6,584,337 B2 | * | 6/2003 | Dumoulin et al. | 600/410 |

FOREIGN PATENT DOCUMENTS

| | | |
|---|---|---|
| DE | 10127930 A1 | 1/2002 |
| EP | 0654675 A1 | 5/1995 |
| EP | 1205760 A2 | 5/2002 |
| JP | H6-304153 | 11/1994 |
| JP | H6-311977 | 11/1994 |
| JP | H8-173396 | 7/1996 |
| WO | WO 02/082996 A1 | 10/2002 |

OTHER PUBLICATIONS

Moran, PR. A flow velocity zeugmatographic interface for NMR imaging in humans. Magnetic Resonance Imaging 1982; 1: 197–203.

Bryant DJ, Payne JA, Firmin DN, and Longmore DB. Measurement of flow with NMR imaging using a gradient pulse and phase difference technique. J Comput Assist Tomogr 1984; 8:588–93.

(Continued)

*Primary Examiner*—Daniel Robinson
(74) *Attorney, Agent, or Firm*—Ziolkowski Patent Solutions Group, SC; Michael A. Della Penna; Carl B. Horton (57) ABSTRACT

The present invention includes a method and apparatus for high sensitivity whole body scanning using MR imaging. The invention includes acquiring MR data as the patient moves through the iso-center of the magnet while providing interactive control for the operator to change scan parameters and table motion and direction. The technique allows efficient whole body scanning for fast screening of abnormalities while allowing operator control during the screening process to interrupt table motion and redirect the speed and direction of the table while also allowing control over the acquisition plane, number of sections imaged, intersection spacing, and the scan location.

33 Claims, 3 Drawing Sheets

OTHER PUBLICATIONS

Van Dijk P. Direct cardiact NMR imaging of heart wall and blood flow velocity. J. Comput Assist Tomogr 1984; 8: 429–36.

Nayler GL, Firmin DN, and Longmore DB. Blood flow imaging by cine magnetic resonance. J Comput Assist Tomogr 1986; 10: 715–22.

Swan JS, Grist TM, Weber DM, Sproat IA, and Wojtowycz MM. MR angiography of the pelvis with variable velocity encoding and a phase–array coil. Radiology 1994; 190: 363–9.

Swan JS, Weber DM, Grist TM, Wojtowycz MM, Korosec FR, and Mistretta CA. Peripheral MR angiography with variable velocity encoding. Work in progress. Radiology 1992; 813–7.

Ehman RL, Felmlee JP. Adaptive technique for high definition MR imaging of moving structures. Radiology 1998; 173: 255–263.

Ho KY, Leiner T, de Haan MW, Kessels AG, Kitslaar PF, and van Engelshoven JM. Peripheral vasculature tree stenoses: evaluation with moving–bed infusion–tracking MR angiography. Radiology 1998; 206: 683–92.

Meaney JF, Ridgway JP, Chakraverty S, Robertson I, Kessel D, Radjenovic A, Kouwenhoven M, Kassner A, and Smith MA. Stepping–table gadolinium–enhanced digital subtraction MR angiography of the aorta and lower extremity arteries; preliminary experience. Radiology 1999; 211: 59–67.

Foo, TKF, Saranathan M, Prince MR, and Chenevert TL. Automated detection of bolus arrival and initiation of data acquisition in fast, three–dimensional, gadolinium–enhanced MR angiography. Radiology 1997; 203: 275–80.

Wilman AH, Riederer SJ, Huston J. 3$^{rd}$, Wald JT, and Debbins JP. Arterial phase carotid and vertebral artery imaging in 3D contrast–enhanced MR angiography by combining fluoroscopic triggering with an elliptical centric acquisition order. Magn. Reson Med. 1998; 40: 24–35.

Riederer SJ, Fain SB, Kruger DG, and Busse RF. 3D–enhanced MR angiography using fluoroscopic triggering and an elliptical centric view order. Int. J. Card Imaging 1999; 15: 117–29.

Prince MR, Chanevert TL, Foo TKF, Londy FJ, Ward JS, Maki JH. Contrast enhanced abdominal MR angiography: Optimization of imaging delay time by automating the detection of contrast material arrival in the aorta. Radiology 1997; 203: 109–114.

Meany, Dr. James FM, Leeds General Infirmary, Leeds UK Moving Bed MRA, The Future of Peripheral Arteriography? *Phillips.*

Kouwenhoven, M., MRA with moving bed imaging, IX International Workshop on Magnetic Resonance Angiography and Introductory Course "New Horizons on MRA and CTA", Valencia, Oct. 7–11, 1997, Book of Abstracts, *The MR Angio Club*, p. 158.

Kruger, DG., Riederer, S.J., Grimm, R.C., Rossman, P.J., Continuously moving table data acquisition method for long FOV contrast–enhanced MRA and whole–body MRI. Magnetic Resonance in Medicine, 47: 224–231 (2002).

K. Liu, B. Rutt, "Sliding Interleaved ky (SLINKY) Acquisition: A Novel 3D MRA Technique with Suppressed Slab Boundary Artifact", JMRI, 8: 903–911 (1998).

K. Liu, B. Rutt, "Systemic Assessment and Evaluation of Sliding Interleaved ky (SLINKY) Acquisition for 3D MRA", JMRI, 8: 912–923 (1998).

K. Liu, "SLINKY: More Understanding, Optimization and Application for High Resonance MRA", ISMRM Seventh Scientific Meeting. 1908, 1999.

K. Liu, Y. Xu, M. Loncar, Artifact Transformation Technique: Shifted Interleaved Multi–Volume Acquisition (SIMVA) for 3D FSE, ISMRM Sixth Scientific Meeting, 1618, 1999.

K. Liu, Y. Xu, M. Loncar "Applications of Shifted–Interleaved Multi–Volume Acquisition (SIMVA) with Suppressed Slab Boundary Artififact", ISMRM Seventh Scientific Meeting, 1618, 1999.

J. Hennig, "Overlapping Section Coverage in Multisection Imaging", JMRI, 3:425–432 (1993).

J. Pipe, "Spatial Encoding and Reconstruction in MRI with Quadratic Phase Profiles", MRM, 33:24–33 (1995).

J. Pipe, "Analysis of Localized Quadratic Encoding and Reconstruction", MRM, 36: 137–146 (1996).

O'Dietrich, J. Hainal, "Extending the Coverage of True Volume Scans by Continuous Movement of the Subject", ISMRMSevemtj Scoemtofoc <eetomg. 1653. 1999.

K.Y. Ho, T. Leiner, M.H. de haan, J.M. A. van Engelshoven, "Gadolinium Optimized Tracking Technique: A new MRA technique for imaging the Peripheral Vascular Tree from Aorta to the Foot using one Bolus of Gadolinium", ISMRM Fifth Scientific Meeting, 203, 1997.

* cited by examiner

WHOLE BODY MRI SCANNING WITH MOVING TABLE AND INTERACTIVE CONTROL

BACKGROUND OF INVENTION

The present invention relates generally to magnetic resonance imaging (MRI), and more particularly to, a method and apparatus for rapid whole body scanning with continuous table motion and image acquisition.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Conventional techniques for whole body imaging or screening using magnetic resonance imaging typically requires multiple positioning and repositioning of the patient to image over a sufficiently large field-of-view (FOV). As a result, whole body screening examinations are often partitioned into two or more separate examinations. In many instances, a patient must return at a later date to complete the examination due to contrast agent uptake and passthrough.

Other so-called moving table techniques include stepping the table through increments and obtaining data at each increment. These techniques do not acquire data while the table is moving, but only between each of the stepped increments.

These techniques are not time-efficient and since the increments must be pre-defined and the acquisitions times accordingly, there is no ability to provide interactive control and the results are prone to gradient warping. Further, attempts at imaging while the table is moving are also prone to gradient warping distortion and require some form of image correction. Such techniques may also require phase encoding in the direction of table motion and require pre-defined knowledge of table speed and/or acceleration/deceleration and are therefore not susceptible to interactive control during image acquisition.

It would therefore be advantageous to design a method and apparatus incorporating a fast technique that is sensitive to abnormalities and allows the physician to quickly survey the entire body to locate regions of abnormalities, such as signal enhancement that is indicative of tumors, with a continuous moving table and with the ability to change the acquisition plane, the pulse sequence, table speed and/or the direction of table motion to thereby focus in and better characterize the abnormality.

SUMMARY OF THE INVENTION

The present invention solves the aforementioned problems by providing a method and apparatus for MR image acquisition that allows continuous scanning while the patient table is in translation and provides interactive control of scan parameters, table motion and/or table direction.

The proposed method allows fast imaging of the whole body for efficient screening for the presence of abnormalities, such as tumors or cancer, in a rapid interactive manner with high sensitivity. The regions identified in the initial screening examination can be further studied in greater detail to identify tumor characteristics and provide the necessary high specificity needed in such exams. The proposed technique involves continuously scanning during table translation and does not rely on generating a large FOV composite image. The interactive control scheme makes efficient use of imaging time by tailoring the acquisition plane and spatial coverage to each anatomical region.

Since the present invention is not limited to generating a single large FOV composite image, it does not need to employ a Fourier transform in a direction of motion. The present technique can therefore incorporate interactive control to make efficient use of the imaging time by tailoring the acquisition plane and spatial coverage to each anatomical region. Scanning parameters can be changed to allow interactive high resolution/tumor specific characterization or inspection of the suspect regions. The present technique allows for continuous variation of imaging parameters such as transmitter and receiver gains and localized shim settings. Since each data acquisition is reconstructed to an individual image, phase variations and gradient non-linearity considerations that are encountered in generating large FOV images are of no consequence in the present invention.

In a preferred embodiment, since the table is in continuous translation specific anatomical regions will only be imaged while moving through the magnet iso-center where the magnetic field homogeneity is most optimal to provide improved signal-to-noise ratio and gradient field linearity. As a result of implementing continuous moving table imaging with interactive control, multiple views of the same anatomical region can be obtained to not only decrease the chances of false positives, but also increase the sensitivity for adequate detection. That is, the proposed technique calls for an interactive scan that allows an operator to enter an initial number of multi-planar sections with an initial intersection spacing, and as the patient traverses through the iso-center of the magnet the operator is allowed to adjust the number of sections imaged, the section spacing, the section scan locations, as well as the acquisition plane. Positions where abnormalities such as lesions are identified, are noted or bookmarked for a more detailed study that can take place immediately, because of interactive table motion and direction control, or can be done after the whole body screen is completed.

A method of acquiring MR images is disclosed which includes positioning a subject on a movable table, entering initial table motion control data and scan parameters, and automatically moving the movable table, based on the initial table motion control data entered, and acquiring MR data based on the scan parameters entered while the movable table is in motion. The method also includes allowing entry and modification of either or both the table motion control data and the scan parameters while automatically moving the table and acquiring MR data.

An MRI apparatus is disclosed to provide highly sensitive whole body screening that includes an MR imaging system having a plurality of gradient coils positioned about a bore of a magnet to impress a polarizing magnetic field. An RF transceiver system and an RF switch is controlled by a pulse module to transmit and receive RF signals to and from an RF coil assembly to acquire MR images. The MRI apparatus also includes a patient table movable under computer control within the bore of the magnet and a computer programmed to receive initial scan parameters and table translation parameters, translate the table, and acquire MR data while the table translates. The computer is also programmed to allow reception of user input during patient table translation and modify translation in response thereto. Additionally, the computer can receive user input of scan parameters and modify the MR data acquisition in response to the modification.

The technique of the present invention is also disclosed with respect to a computer program stored on a computer readable storage medium which, when executed by a computer, causes the computer to move a patient table through an MR scanner and simultaneously acquire MR data while the patient table is moving. The computer program also has instructions that can cause the computer to allow and receive user input and in response thereto, manipulate patient table speed, patient table direction, or various scan parameters in real-time, defined herein as either real-time or near real-time, as those skilled in the art will readily recognize.

In accordance with another aspect of the present invention, a method of identifying a tumor in a patient is disclosed. The method includes placing the patient on a movable table, translating the movable table and acquiring MR data as the patient moves through a magnetic field. This method also includes reconstructing MR images of patient anatomy as the movable table is translating and analyzing the MR images. If an area of interest is identified for further study, the process includes returning the movable table such that the area of interest is within the magnetic field and modifying MR data acquisition parameters in real-time. Images can then be acquired that are either of higher resolution or in a different plane to allow further analysis and characterization of the tumor.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

Figure 1:
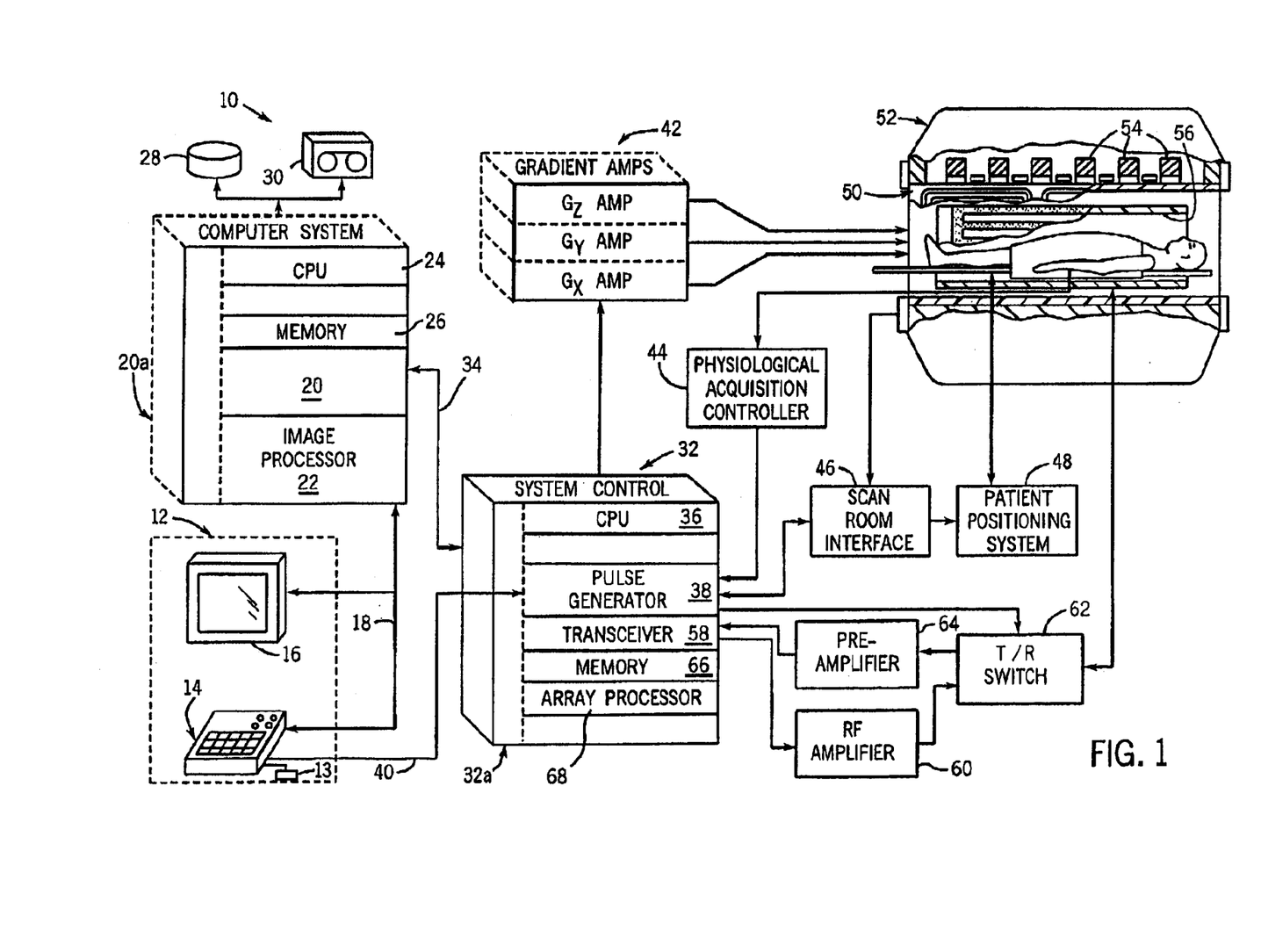
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription and patient table speed and direction control.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention includes a method and system for acquiring MR image data for use with the above-reference MRI system, or any similar equivalent system for obtaining MR images.

Figure 2:
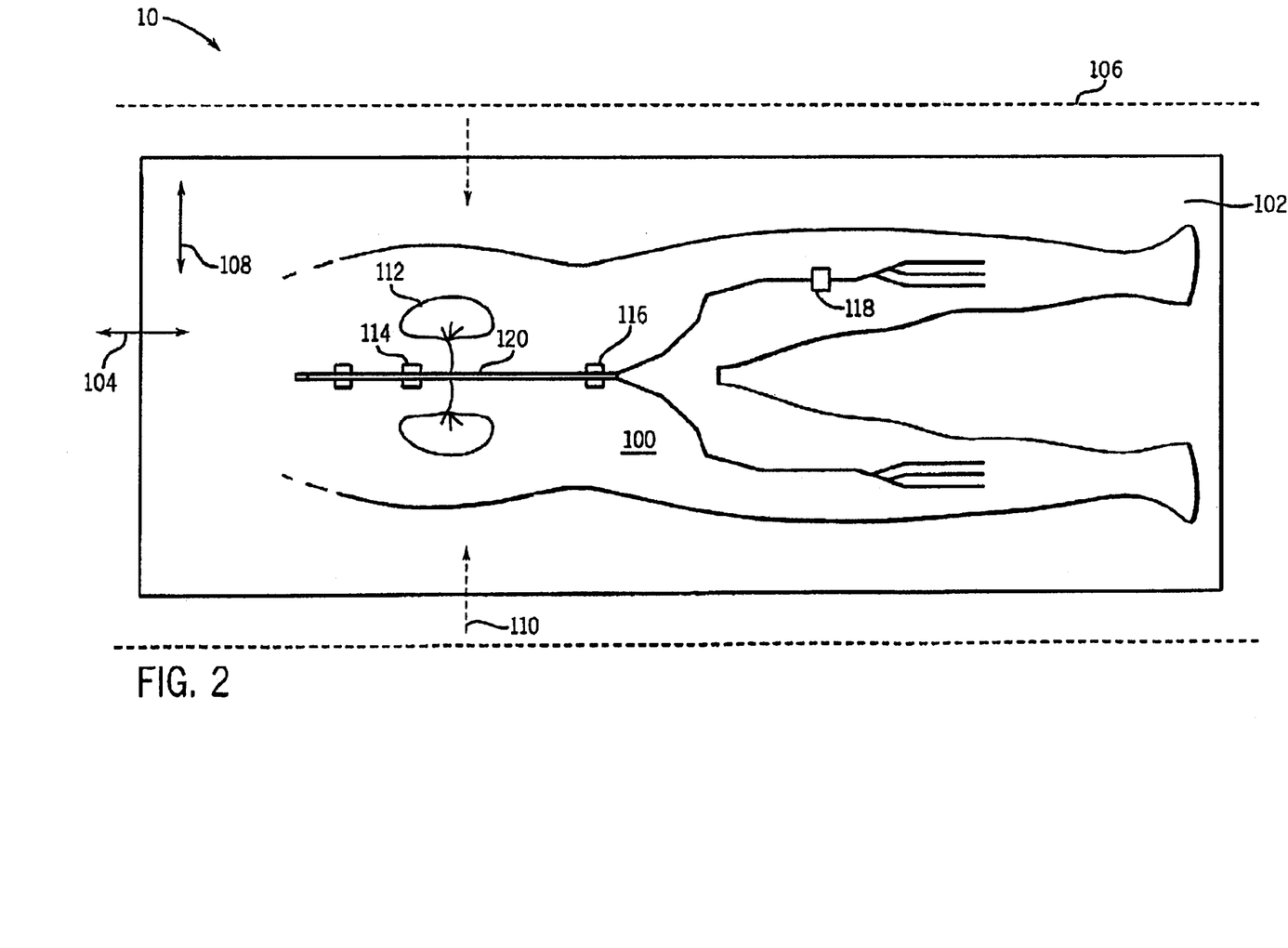
FIG. 2 is an enlarged top planar view of the patient table of FIG. 1 with depiction of a patient thereon and being movable under computer control in accordance with the present invention.

Referring to FIG. 2, a patient 100 is shown supported on a computer controlled, movable table 102 which is controlled by CPU 36 of system control 32 of FIG. 1. The movable table 102 may be moved or translated fore and aft as indicated by arrow 104 through the bore of magnet 106 in the MRI apparatus 10. Thus, patient 100 may be selectively positioned within the bore of main magnet 106 and the motion of the table is under computer control along axis 104. Additionally, the system can be designed to allow movement of table 102 laterally as indicated by arrows 108.

The present invention is particularly sensitive to locating tumors or tumor markers and allows a physician or clinician to quickly survey the entire body to locate regions of signal enhancement that is indicative of tumors, and allow modifying the acquisition plane and pulse sequence to characterize the tumor or lesion. Such evaluation of abnormal regions, such as tumors and lesions, requires both the detection of the abnormality and the proper delineation of its anatomic extent (i.e. staging). Although this can be achieved using the inherent MR properties of tissue, such as $T_1$ or $T_2$ weighting, it is often desirable to use contrast agents to provide sufficient contrast-to-noise ratio for confident diagnostic evaluation of abnormal tissue. It is generally known that such contrast media provides improved contrast through vascularity differences between abnormal and normal regions. When surveying a patient for possible tumors, it is desirable to acquire MR image data of the entire length of the patient. Such whole body imaging is typically conducted by moving a region of interest to the magnet iso-center 110, bringing the table to a stop, and then acquiring MR data. After acquiring an entire set of data for that anatomical section of the patient, the patient would be translated to a second position, stopped, and data again would be acquired. A certain amount of overlap between the scan stations is typically desired to enable effective registration of images from one scan station to the next to form a single image covering the entire extent of the imaging region for all stations. In the example of FIG. 2, the pulmonary system 112 of patient 100 is in the iso-center 110 of magnet 106. Monitors 114, 116, and 118 can be placed in close proximity to vessel 120 to monitor the travel of a contrast agent through patient 100, if desired. However, the present invention is not limited to the use of bolus detection and does not require contrast agent, although utilizing contrast enhancement is a current preferred embodiment of one aspect of the present invention.

Further, it is preferred that all imaging be performed at the magnet iso-center while the table 102 is translated to allow imaging in the optimal or "sweet spot" of the magnet to reduce image artifacts. The technique of the present invention includes continuously scanning while the table is in translation and can perform multi-planar fast imaging.

Figure 3:
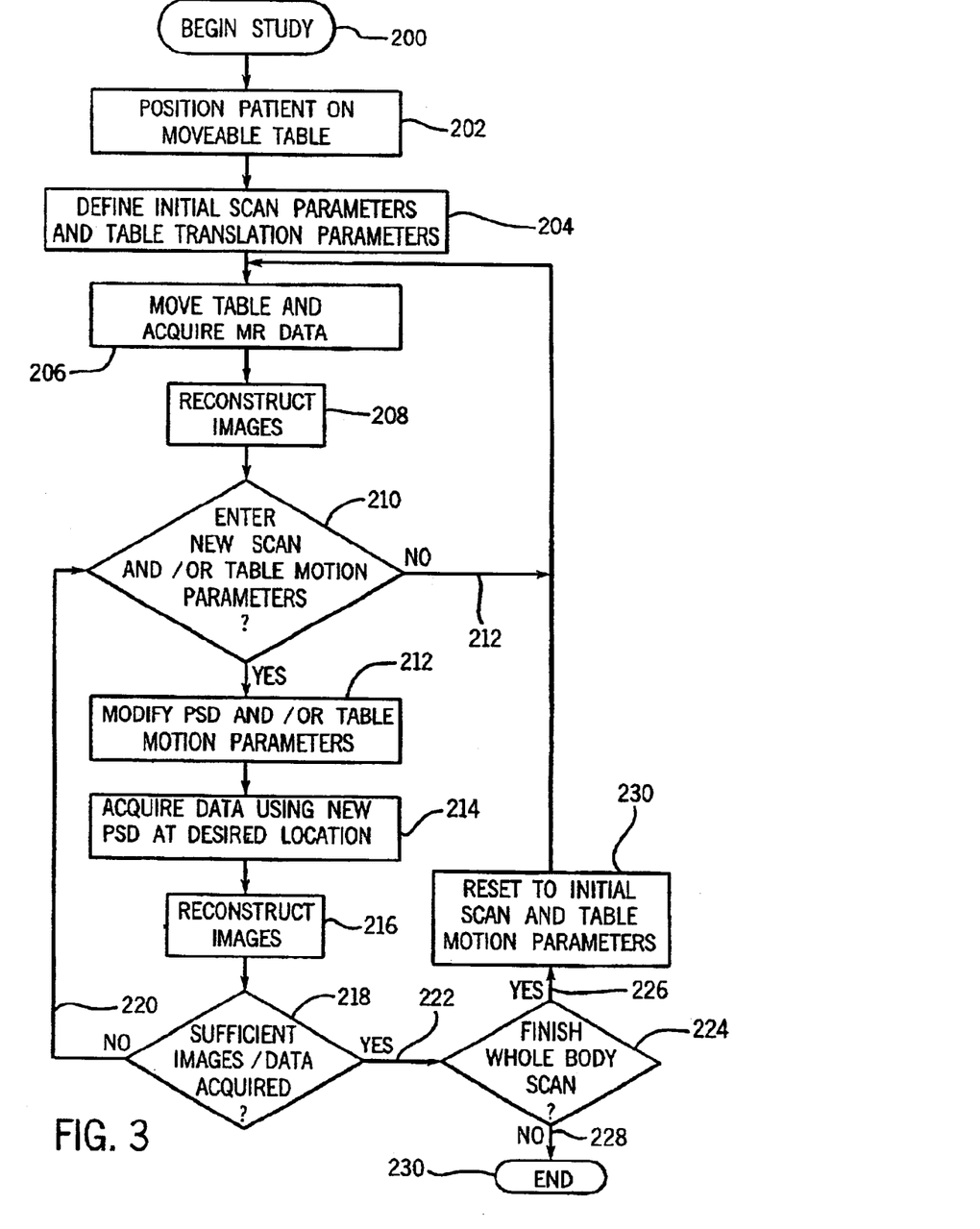
FIG. 3 is a flow chart of a technique of the present invention for use with the apparatus of FIGS. 1 and 2.

Referring to FIG. 3, an exemplary flow chart depicts a method according to the present invention that can be implemented in a computer program for use with the MR apparatus shown in FIGS. 1 and 2. After acquiring patient data and initializing the MR apparatus 200, the patient is positioned on the movable table 202. Initial scan parameters and table motion parameters are then defined at 204. Initially, the multi-planar fast imaging sequence includes an operator determined plane through an anatomic region of interest. Under computer control, the table is then moved and MR data is acquired at 206. The images are immediately reconstructed at 208 for evaluation to enable interactive control. That is, after acquiring images using the operator determined plane, a predefined number of multi-planar sections, and initial inter-section spacing, the operator is able to adjust the number of sections imaged, the section spacing, the section scan locations, as well as the acquisition plane in virtual real-time. The operator is given the opportunity to enter new scan parameters and/or table motion parameters at 210. Table motion parameters can be entered via any convenient input device, such as a joy stick, mouse, track ball, etc. as described with reference to input device 13, FIG. 1.

If the operator chooses to continue to scan 210, 212, the table will continue to move, preferably at a constant speed, while MR data is acquired and as the patient traverses through the iso-center of the magnet. Positions at which abnormalities are identified are noted or bookmarked for a more detailed study either at that moment or after the whole body screen is completed. If the operator elects to perform the detailed study immediately, new scan data and/or table motion parameters can be entered at 210 to modify the pulse sequence and/or table movement 212. In this manner, since the table translation is under operator control via the input device 13, FIG. 1, the operator is given sufficient degrees of freedom to control the speed and direction of table motion. The operator can then tailor scanning for areas of contrast enhanced tumors by having control over the acquisition plane, number of sections image, inter-section spacing, and the scan location. This technique allows the operator to tailor scanning, while accounting for individual patient variations and specific disease characteristics. After acquiring data in the area of abnormality 214 and reconstructing images for analysis 216, the operator is given the ability to modify the scan parameters and/or the table motion again 218, 220. Once sufficient images have been acquired 218, 222, the operator can then decide whether to finish the whole body scan 224, 226, in which case the scan and table parameters are reset 230 and whole body scanning can resume at 206, or the operator can elect to conclude the examination 224, 228 and end the study 230.

When the specific areas of abnormality, such as tumor enhancement, have been identified, the operator can return the table to specific locations and acquire high spatial resolution functional images to characterize the type of abnormality using known methods such as contrast material uptake, with a corresponding further administration of contrast agent or tumor specific markers, diffusion, multi-parametric imaging, or any other characterization method.

Accordingly, the present invention allows fast screening of the entire body for the presence of abnormalities such as tumors or cancer in a rapid interactive manner with high sensitivity. In order to provide the corresponding high specificity information, regions identified in the screening examination can be studied in greater detail to provide abnormality characteristics.

The proposed technique does not rely on methods of generating large FOV composite images and therefore can tailor the acquisition plane in spatial coverage for each anatomical region. Such an interactive system makes efficient use of imaging time by providing a system that allows efficient screening while allowing the operator to hone into a specific region of interest in real-time. In other words, the operator is given the ability to interrupt a whole body scan when an abnormality is indicated and reverse table motion to acquire high resolution images of the abnormality immediately. Alternatively, or in addition, the operator also has the option of acquiring images in a different plane with or without higher resolution or with different section spacing or even with a different pulse sequence. The combination of options is limitless and the present invention is not limited to any particular set of scan parameters. The present invention is particularly advantageous when a contrast agent is used in conjunction with bolus detection so that the anatomical region can be analyzed when the contrast agent uptake is at a high level. Further, unlike composite image techniques, the interactive continuous table motion technique of the present invention allows for continuous variation of imaging parameters such as transmitter and receiver gains and localized shim settings. Since each set of data is reconstructed as its own image, phase variations and gradient non-linearity considerations that are encountered in generating large FOV images become irrelevant.

With continuous moving table imaging, together with real-time table motion control, multiple views of the same anatomical region can be obtained and any specific anatomical region of the body will always move through the magnet iso-center where the magnetic field homogeneity is the most optimal. The ability to acquire multiple views of the same anatomical region decreases the chances of a possible false positive and also increases the sensitivity for detection of abnormalities.

Exemplary studies were conducted on a GE Medical Systems 1.5 Tessla CV/i MR scanner with high performance gradients. Patients were scanned with pulse sequences that continuously acquired and reconstructed data in real-time while the patient was in continuous translation. Multiple 2D sections were continuously acquired while table speed was controlled between 0.5 and 10 cm/sec. However, the preferred speed of translation was found to be 0.5 cm/sec for optimal spatial coverage and image acquisition time. While it is believed that the present technique will render itself useful with many pulse sequence types, including 3D imaging, initial investigation found satisfactory results with both an inversion recovery fast gradient echo (IR-prep) and a fast imaging employing steady-state acquisition (FIESTA) acquisition. In the IR-prep sequence, TI times of between 400–600 msec. were used with a TR time of 6.3 msec., a TE time of 2.1 msec., and a flip angle of 30°. Other scan parameters that provided satisfactory results included an FOV of 36–42 cm, sections of 7–10 mm, a matrix of 256×160 with 0.5 NEX and a receiver bandwidth of plus/minus 31.25 kHz. In all cases, fat suppression is a user selectable option. With fat suppression enabled, a spectrally selective inversion pulse was used with a TI of 20 msec. For the FIESTA sequences, scan parameters were similar but with a TR/TE/flip=3.7 msec./1.5 msec./45°, along with a 1.0 NEX and plus/minus 125 kHz receiver bandwidth. An intermittent fat suppression RF pulse was applied every 40 RF excitations for fat suppression.

Imaging data was acquired continuously with the table moving at 0.5 cm/sec from the neck to the lower leg using IR-prep sequences and FIESTA before and after intravenous contrast in several subjects. Axial scans required a mean of 3.2 minutes to cover the required anatomy whereas coronal acquisitions required a mean of only 1.5 minutes. Axial scans were non-overlapping and demonstrated occasional slice heterogeneity but were remarkably free of motion artifacts. Coronal scans were considerably overlapped allowing multiple views of the same region of interest. Additional intravenous contrast improved overall signal and intensity. This technique provides screening images with rapid multi-planar coverage of the whole body and continuous scanning of the iso-center of the magnet provides minimal motion artifacts.

Accordingly, the present invention includes a method of MR image acquisition that includes positioning a subject on a movable table, entering table motion control data and scan parameters, and automatically moving the movable table based on the table motion control data entered. The method also includes acquiring MR data based on the scan parameters entered while the movable table is in motion and allowing entry and modification of either or both the table motion control data and the scan parameters while automatically moving the table and acquiring MR data.

The invention also includes an MRI apparatus for whole body screening that includes an MRI system having a number of gradient coils positioned about a bore of a magnet to impress a polarizing magnetic field and an RF transceiver system and an RF modulator controlled by a pulse control module to transmit RF signals to an RF coil assembly to acquire MR images. The MRI apparatus also includes a table movable under computer control within the bore of the magnet and a computer programmed to receive initial scan parameters and table translation parameters and translate the patient table and acquire MR data while the patient table translates. The computer is also programmed to allow reception of user input during patient table translation and modify translation in response thereto and allow reception of user input of scan parameters and modify MR data acquisition in response thereto.

The invention also includes a computer program stored on a computer readable storage medium that can cause the computer to move a patient table through an MR scanner and simultaneously acquire MR data while the patient table is moving and allow user input and in response thereto, manipulate at least one of the patient table speed, direction, and scan parameters in real-time.

The invention also includes a clinical process of identifying a tumor in a patient that includes placing the patient on a movable table, translating the movable table and acquiring MR data as a patient moves through a magnetic field. The process further includes reconstructing MR images of patient anatomy as the movable table is translating and analyzing the MR images. If an area of interest is identified for further study, returning the movable table such that the area of interest is in within the magnetic field and modifying the MR data acquisition parameters in real-time to acquire MR data with either a higher resolution or of a differing plane to further analyze the area of interest.

The present invention has been described in terms of the preferred embodiment, and it is recognized that equivalents, alternatives, and modifications, aside from those expressly stated, are possible and within the scope of the appending claims.

What is claimed is:

1. A method of MR image acquisition comprising:
positioning a subject on a movable table;
entering initial scan parameters;
automatically moving the movable table during MR data acquisition;
acquiring MR data based on the scan parameters entered; and allowing modification of at scan parameters while automatically moving the table and acquiring MR data.

2. The method of claim 1 further comprising providing interactive control of table motion and scan parameters that include control over and adjustment of at least one of: speed of the movable table, direction of table motion, and pulse sequence for MR data acquisition.

3. The method of claim 1 wherein the step of acquiring MR data includes ability to continuously scan while the movable table is in translation using a multi-planar fast imaging pulse sequence.

4. The method of claim 3 further comprising the step of initially selecting a desired plane for MR data acquisition through an anatomic region of interest, and as the subject traverses through a magnet iso-center, allowing operator adjustment of at least one of a number of sections imaged, section spacing, section scan locations, and imaging plane.

5. The method of claim 1 further comprising providing an ability to interrupt scanning after identifying an abnormality of interest, reversing the movable table and acquiring high spatial resolution image data.

6. The method of claim 5 wherein the abnormality of interest is a tumor and further comprises the steps of acquiring functional images and characterizing the tumor using one of contrast media uptake, diffusion, and multi-parametric imaging.

7. The method of claim 1 further comprising tailoring acquisition plane and spatial coverage to each anatomical region desired during MR image acquisition in real-time.

8. The method of claim 1 further comprising allowing continuous variation of imaging parameters including transmitter/receive gains and localized shimming.

9. The method of claim 1 further comprising obtaining multiple images of a same anatomical region to decrease false positive possibilities.

10. An MRI apparatus with sensitive whole body screening ability comprising:
a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images;
a table movable under computer control within the bore of the magnet;
a computer programmed to:
receive initial scan parameters and table translation parameters;
translate the table;
acquire MR data while the table translates;
allow reception of user input during table translation and if so received, modify translation in response thereto; and
allow reception of user input of scan parameters during table translation and if so received, modify MR data acquisition in response thereto.

11. The MRI apparatus of claim 10 wherein MR data is acquired continuously during table translation.

12. The MRI apparatus of claim 10 wherein table translation is approximately 0.5 cm/sec. and scan times are approximately one second to thereby reduce motion artifacts.

13. The MRI apparatus of claim 10 wherein the computer is further programmed to allow user-selectable fat suppression and when selected, apply an intermittent fat suppression RF pulse.

14. The MRI apparatus of claim 10 wherein the computer is further programmed to monitor flow of an intravenous contrast agent.

15. The MRI apparatus of claim 10 wherein the computer is further programmed to acquire data of a region of abnormality in multiple planes in real-time.

16. The MRI apparatus of claim 10 wherein the computer is further programmed to allow manipulation of at least one of image obliquity, table speed, table direction, and pulse sequence parameters such as inversion time, flip angle, and sequence type in real-time.

17. The MRI apparatus of claim 10 wherein the computer is further programmed to acquire functional images and allow characterization of lesions in real-time.

18. The MRI apparatus of claim 10 wherein the computer is further programmed to vary transmitter gain, receiver gain, and shimming on demand by a user.

19. A computer readable storage medium having stored thereon a computer program comprising instructions which, when executed by a computer, cause the computer to:
move a patient table through an MR scanner and simultaneously acquire MR data; and
allow user input during patient table movement and MR data acquisition and in response thereto, manipulate at least one of patient table speed, direction, and scan parameters.

20. The computer readable storage medium of claim 19 wherein the computer is further caused to acquire data of an abnormality in various planes and reconstruct functional images to characterize the abnormality in real time.

21. The computer readable storage medium of claim 19 wherein the computer is further caused to allow manipulation of at least one image obliquity, table speed, table direction, and pulse sequence parameters, such as inversion time, flip angel, and sequence type and wherein the computer is further caused to vary transmitter gain, receiver gain, and shimming on demand by a user.

22. The computer readable storage medium of claim 19 wherein the computer is further caused to allow user-selectable fat suppression and when selected, apply an intermittent fat suppression RF pulse.

23. A method of identifying a tumor in a patient comprising:
placing a patient on a movable table;
translating the movable table and acquiring MR data as the patient moves through a magnetic field;
reconstructing MR images of patient anatomy as the movable table is translating;
analyzing the MR images and if an area of interest is identified for further study, returning the movable table such that the area of interest is within the magnetic field and modifying MR data acquisition parameters in real-time; and
acquiring one of higher resolution MR data and differing plane MR data to allow further analysis of the area of interest.

24. The method of claim 23 further comprising injecting a contrast media to monitor contrast uptake by various anatomy.

25. The method of claim 23 further comprising applying fat suppression for tumor identification.

26. The method of claim 23 wherein MR data acquisition is performed at magnet iso-center to optimize resolution of MR data acquired of a moving patient.

27. The MR apparatus of claim 10 wherein the computer applies one of an inversion recovery fast gradient echo (IR-prep) and a fast imaging employing steady-state acquisition (FIESTA) pulse sequence.

28. The method of claim 1 further comprising the steps of entering initial table motion control data and allowing modification of the initial table motion control data while moving the table and acquiring MR data.

29. The computer readable storage medium of claim 19 wherein the computer is further caused to manipulate patient table speed during patient table movement and MR data acquisition.

30. A method of MR image acquisition comprising:

positioning a subject on a movable table;

entering initial table motion control data and scan parameters;

automatically moving the movable table based on the table motion control data entered;

acquiring MR data based on the scan parameters entered while the movable table is in motion;

allowing modification of at least one of the initial table motion control data and the scan parameters while automatically moving the table and acquiring MR data; and providing an ability to interrupt scanning after identifying an abnormality of interest, reversing the movable table and acquiring high spatial resolution image data.

31. The method of claim 28 wherein the abnormality of interest is a tumor and further comprises the steps of acquiring functional images and characterizing the turner using one of contrast media uptake, diffusion, and multi-parametric imaging.

32. A method of MR image acquisition comprising:

positioning a subject on a movable table;

entering initial table motion control data and scan parameters;

automatically moving the movable table based on the table motion control data entered;

acquiring MR data based an the scan parameters entered while the movable table is in motion;

allowing modification of at least one of the initial table motion control data and the scan parameters while automatically moving the table and acquiring MR data; and tailoring acquisition plane and spatial coverage to each anatomical region desired during MR image acquisition in real-time.

33. A method of MR image acquisition comprising;

positioning a subject on a movable table;

entering initial table motion control data and scan parameters;

automatically moving the movable table based on the table motion control data entered;

acquiring MR data based on the scan parameters entered while the movable table is in motion;

allowing modification of at least one of the initial table motion control data and the scan parameters while automatically moving the table and acquiring MR data; and allowing continuous variation of imaging parameters including transmitter/receive gains and localized shimming.

* * * * *

UNITED STATES PATENT AND TRADEMARK OFFICE
CERTIFICATE OF CORRECTION

PATENT NO. : 6,963,768 B2
DATED : November 8, 2005
INVENTOR(S) : Ho et al.

It is certified that error appears in the above-identified patent and that said Letters Patent is hereby corrected as shown below:

Column 11,
Line 25, delete "turner" and substitute -- tumor --.

Signed and Sealed this

Thirty-first Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,963,768 B2 Page 1 of 1
APPLICATION NO. : 10/063829
DATED : November 8, 2005
INVENTOR(S) : Ho et al.

It is certified that error appears in the above-identified patent and that said Letters Patent is hereby corrected as shown below:

On the cover page, column 1, under "Assignee:" after "General Electric Company, Milwaukee, WI (US)", add -- ; Uniformed Services University of Health Sciences, Department of Defense, United States Government, Bethesda, MD (US) --.

Signed and Sealed this

Twenty-third Day of January, 2007

JON W. DUDAS
*Director of the United States Patent and Trademark Office*